United States Patent [19]

Kent et al.

[11] Patent Number: 4,936,852

[45] Date of Patent: Jun. 26, 1990

[54] TEMPOROMANDIBULAR MINI CONDYLE PROSTHESIS

[75] Inventors: John N, Kent, Metaire, La.; Charles A. Homsy, Houston, Tex.

[73] Assignee: Vitek, Inc., Houston, Tex.

[21] Appl. No.: 180,465

[22] Filed: Apr. 12, 1988

Related U.S. Application Data

[63] Continuation-in-part of Ser. No. 939,558, Dec. 9, 1986, Pat. No. 4,778,472, which is a continuation-in-part of Ser. No. 728,820, Apr. 30, 1985, abandoned.

[51] Int. Cl.$^5$ .............................................. A61F 2/30
[52] U.S. Cl. ........................................ 623/18; 623/16
[58] Field of Search ..................... 623/16, 17, 18, 20, 623/22, 23

[56] References Cited

U.S. PATENT DOCUMENTS

| | | | |
|---|---|---|---|
| 3,178,728 | 4/1965 | Christensen | 623/18 |
| 3,579,643 | 5/1971 | Morgan | 623/18 |
| 4,693,722 | 9/1987 | Wall | 623/18 |
| 4,778,472 | 10/1988 | Homsy et al. | 623/18 |
| 4,787,908 | 11/1988 | Wyss et al. | 623/18 X |

Primary Examiner—Alan W. Cannon
Attorney, Agent, or Firm—Michael P. Breston

[57] ABSTRACT

The prosthetic mini-condyle is for use with a prosthetic glenoid fossa. The mini-condyle covers an excised natural condyle having a superior cut surface and a lateral cut surface. The mini-condyle has a superior, convexoplanar articular face and an inferior flat face. A shank extends inferiorly from the inferior face and is adapted to become secured to the lateral cut surface. The flat interior face is adapted to abut against the superior cut surface. Preferably, a porous bicompatible coating is bonded to the inferior face of the condyle and to the medial face of the shank.

15 Claims, 1 Drawing Sheet

TEMPOROMANDIBULAR MINI CONDYLE PROSTHESIS

This application is a continuation-in-part application of patent application Ser. No. 06/939,558, filed Dec. 9, 1986, (now U.S. Pat. No. 4,778,472), which was a continuation-in-part of patent application Ser. No. 06/728,820, filed Apr. 30, 1985 that has since been abandoned.

BACKGROUND OF THE INVENTION

1. Field of the Invention

This invention relates to a mini-condyle prosthesis for use with a glenoid fossa prosthesis.

2. Description of the Prior Art

The natural temporomandibular joint (TMJ) consists of the glenoid fossa, the condyle of the mandible, the disc, and muscle attachments.

Patients with severe destruction of the TMJ anatomy from rheumatoid arthritis, osteoarthritis, tumors, and trauma all manifest significant functional impairment and often pose difficult challenges in TMJ reconstruction.

In said parent application, Ser. No. 939,558, is described a condyle prosthesis for use with a glenoid fossa prosthesis. This prior condyle prosthesis has been used by oral surgeons for restoring a substantial bone loss, as well as a small bone loss, in the condyle.

To implant the prior condyle prosthesis, the surgeon needs to make two incisions: a vertical incision in front of the ear, and a lateral incision below the angle of the jaw.

After the masseter and medial ptyergoid muscles are detached from the mandible, and after unavoidable damage to local tissue, the surgeon excises the diseased condyle at the neck and below the attachment thereto of the lateral ptyergoid muscle.

Such a surgical procedure for using the prior condyle prosthesis is beneficial to a patient who requires a restoration of a substantial bone loss in the condyle. However, excising the condyle at the neck and below the attachment thereto of the lateral ptyergoid muscle may be detrimental and inefficient for a patient who requires a restoration of only a small bone loss in the condyle above the attachment of the lateral ptyergoid muscle to the condyle. This inefficiency includes the loss of a useful portion of the natural condyle.

Also, because of the lateral incision below the angle of the jaw, the patient may require intensive and prolonged oral cavity and TMJ rehabilitation until damaged local tissues heal and the masseter and medial ptyergoid muscles reattach to the mandible.

It is an object of this invention to provide a mini-condyle prosthesis which does not require an incision below the angle of jaw.

It is a further object of this invention to provide a mini-condyle prosthesis which is suitable for patients who have sustained any amount of loss of condyle, but particularly a small loss of condyle.

SUMMARY OF THE INVENTION

The prosthetic mini-condyle is for use with a prosthetic glenoid fossa. The prosthetic fossa covers the natural glenoid fossa and articular eminence. The prosthetic fossa defines an articular, concavo-planar cavity.

The mini-condyle is adapted in the TMJ to cover a partially or totally excised natural condyle having a superior cut surface and a lateral cut surface over the remaining condylar head or neck. The superior cut surface is above, at, or below the attachment of the ptyergoid muscle to the natural condyle. The mini-condyle preferably has a superior, convexo-planar articular face and an inferior flat face. A shank extends inferiorly from the inferior face and is adapted to become secured to the lateral cut surface with screws or wires. The flat inferior face is adapted to abut against the superior cut surface. A porous biocompatible coating or layer is preferably bonded to the inferior face of the condyle and to the medial face of the shank.

The method of implanting the prosthetic mini-condyle on the mandibular bone involves determining the extent of the deteriorated natural condyle, making a first planar cut on the superior side of the remaining condyle stump, making a second planar cut perpendicular to the first cut and on the lateral side of the condyle or neck stump, thereby establishing a condylar stump having a superior cut surface and a lateral cut surface. The inferior face of the condyle is abutted against the superior cut face on the stump, and the shank is secured to the lateral cut surface.

DESCRIPTION OF PREFERRED EMBODIMENTS

Figure 1:
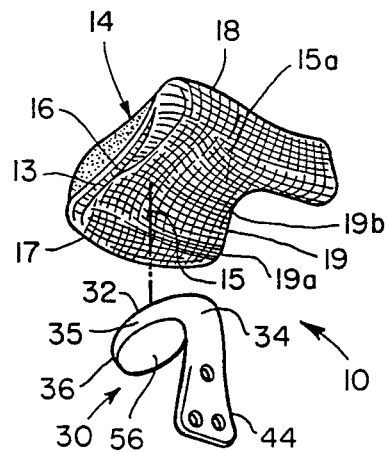
FIG. 1 is an exploded, perspective view of one embodiment of the novel mini-condyle prosthesis, and of the glenoid fossa prosthesis described in said parent patent application.
Figure 2:
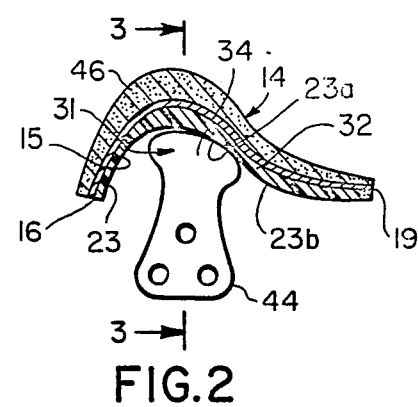
FIG. 2 is a rear side plan elevational view of the mini-condyle prosthesis of FIG. 1, when the jaws are near full engagement, and is a sectional view of the fossa prosthesis.
Figure 3:
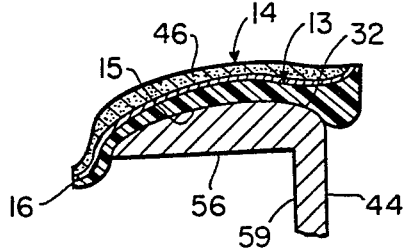
FIG. 3 is a sectional view of the glenoid fossa prosthesis taken on line 3—3 of FIG. 2, and is a front view of the mini-condyle prosthesis.

A brief description of a total TMJ prosthesis will facilitate the understanding of the present invention.

The temporomandibular joint or TMJ is formed between the temporal bone and the mandibular bone. The TMJ includes a glenoid fossa in the inferior surface of the temporal bone, and a condyle which is the extension of the ramus within the mandibular bone. Between the glenoid fossa and the condyle is a moving meniscus (not shown) which serves to protect and lubricate the joint.

The functionally unique feature of the TMJ is its unusual combination of a sliding movement and a finely balanced hinge movement with a high degree of anatomical precision.

Functional TMJ integrity, efficiency, and performance depend on the synchronized movements of a group of muscles which perform their functions synergistically. The mandibular elevator muscles, which close the mandible, include the coordinated function of the masseter, temporal, and medial ptyergoid muscles (not shown). The mandibular depressor muscles, which open the mandible, include the external ptyergoid and the suprahyoid muscles. Protrusion of the mandible is performed by the masseter, internal ptyergoid, and the external ptyergoid muscles. Retrusion of the mandible is accomplished by the temporal and digastric muscles.

When all these muscles are functionally intact, the right and left TMJs move in harmony, which is essential for the proper occlusion of the teeth. But, when these muscles and surrounding tissues become detached and/or injured in accidents, or in intensive surgery involving the installation of the prior condyle prosthesis, disclusion or malocclusion of the teeth may occur at least temporarily.

To facilitate the description, the same numerals, as used in said parent patent application, will be used herein to designate the same or similar parts.

The novel mini-condyle prosthesis, generally designated as 30 (FIGS. 1-3, 7), is designed for use with a glenoid fossa prosthesis. A preferred glenoid fossa prosthesis, generally designated as 14, is fully described in said parent application, Ser. No. 06/939,558, filed Dec. 9, 1986, and which is incorporated herein by reference.

The mini-condyle prosthesis 30 comprises a head 31, which is preferably provided with a critical load-transmitting, superior convexo-planar, articular face 32, and with an inferior flat face 56 from which downwardly extends a shank 44.

A heel 34 extends backwardly and a toe 36 extends forwardly from fossa face 32. An oval sole 35 extends rearwardly from face 32 to inferior face 56 and smoothly blends at its opposite ends with heel 34 and toe 36.

Fossa prosthesis 14 is made of a superior layer 46 of PROPLAST (a registered trademark of Vitek, Inc.), which is a tissue ingrowth-promoting material (e.g., a composite of polytetrafluoroethylene polymer and aluminum oxide or synthetic hydroxylapatite), and of an inferior plate 13 of fluorinated ethylene propylene or ultra high molecular weight polyethylene polymer having an embedded polyamide mesh reinforcement therein.

Plate 13 is shaped to fully cover the natural fossa cavity including the adjoining natural articular eminence. Plate 13 has an inferior fossa cavity 15 which is defined by posterior rim 16, medial rim 17, lateral rim 18, and anterior eminence rim 19.

Medial rim 17 smoothly joins posterior rim 16 and likewise projects inferiorly to cover the medial aspect of the natural glenoid fossa and the adjoining articular eminence. The anterior eminence rim 19 has an apex 19a and projects anteriorly and obliquely superiorly to cover the articular eminence. Rim 19 is relieved at 19b to conform to the junction between the natural zygoma and the natural articular eminence. Lateral rim 18 extends superiorly to and is shaped to fit along the lateral extension of the zygoma.

Rim 18 usually receives screws (not shown) by means of which fossa prosthesis 14 is initially attached to the zygoma. The tissue-ingrowth promoting porous layer 46 provides permanent postoperative fixation to the apposite surface of the natural fossa cavity.

Fossa cavity 15 has a load-bearing, articular surface defined by a relatively deep concave portion 23 (FIG. 2), which begins posteriorly, extends superiorly to an anteriorly-superiorly located concavo-planar portion 23a, and extends anteriorly to a convexo-planar portion 23b. Fossa cavity 15, anterior eminence rim 19, medial rim 17, and posterior rim 16 are shaped to offer minimum friction to the complex movements of convexo-planar, articular face 32 of condyle 30.

When articulating the mandible from closed bite position to nearly open bite, condylar face 32 moves forwardly on deep concave fossa surface 23, then the planar portion of face 32 slides, while exerting very strong pressure, over the planar portion of surface 23a, and then face 32 moves toward the convex portion of the convexo-planar surface 23b.

Figure 4:
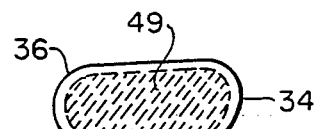
FIG. 4 shows the optimum planar contact surface between the condyle and the fossa prostheses, when the condyle exerts the maximum pressure against the articular surface of the fossa cavity.

When the TM joint is within mid-opening to closed bite position (FIG. 2), articular convexo-planar condylar face 32 of condylar head 31 engages articular concavo-planar surface 23a of fossa cavity 15 and establishes therewith a relatively wide planar contact area 49 (FIG. 4), which minimizes the stress (kg/cm$^2$) transmitted between the fossa and condylar prostheses 14 and 30, respectively, and provides for even load distribution between their engaged planar sliding surfaces.

The condylar face 32 and surface 23a of fossa cavity 15 are shaped to maximize the extent of the contact area 49 therebetween (FIG. 4), as condylar head 31 translates and rotates within fossa cavity 15. A wide contact area 49 between the mating planar surfaces is desired to allow for an even load distribution and to minimize wear and stress concentrations.

The method of implanting the novel mini-condyle prosthesis 30 (FIG. 9) requires only one incision in front of the ear. The usual second lateral incision below the angle of the jaw is not employed.

After determining the extent of the deteriorated natural condyle, the surgeon makes a first planar cut 52 on the superior side of the remaining condyle stump, then a second planar cut 51 is made perpendicular to the first cut 52 and on the lateral side 55 of the condyle or neck stump. Cuts 51,52 are made without the need to detach the masseter and the medial ptyergoid muscles from the mandible. What remains after cuts 51,52 are made is a condylar stump 50 having a superior cut surface 54 and a lateral cut surface 55.

Because such excision may amount to a minimum reduction in the bony mass of the natural condyle and to a minimum derangement to muscles and tissue, and further because the need for making a second incision below the angle of the jaw is avoided, the patient is likely to experience much less pain and rapid postoperative TMJ recovery in regard to mandibular function, occlusal teeth behavior, ligamentous tissue strength, and enhanced muscles of mastication.

The surgeon is provided with mini-condyles 30 having different heights, but if the height of condylar head 31 is insufficient, the surgeon can control, within a small range, the inferior surface of porous layer 46 of fossa 14, thereby lowering the articular surface of fossa cavity 15.

Shank 44 of condyle 30 can assume various configurations depending on the extent of lateral cut face 55 on stump 50. Shank 44 can be secured to lateral face 55 by a number of surgical screws 57, by wires, or by other means.

In a simplified embodiment of condyle 30 (FIGS. 3,9), the flat inferior face 56 of condylar head 31 and the medial face 59 of shank 44 are shaped to directly engage superior cut stump surface 54 and lateral shank face 59, respectively. Thus face 56 is abutted against superior cut face 54, and medial face 59 is abutted against and is secured to lateral cut surface 55 of stump 50.

Figure 5:
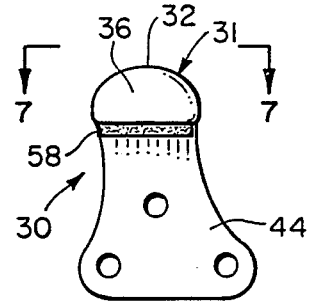
FIG. 5 is a front side elevational plan view of a mini-condyle prosthesis, as shown in FIG. 1, and in addition includes a porous coating on the inferior face thereof.
Figure 9:
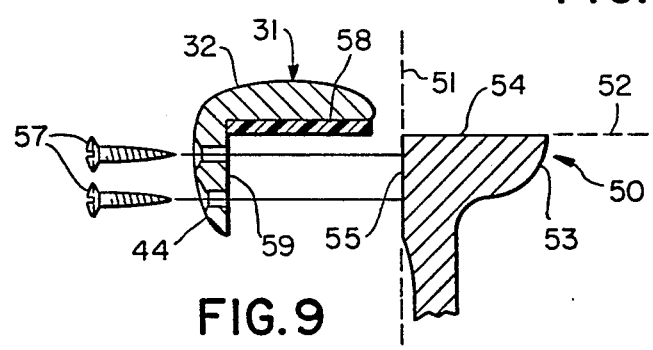
FIG. 9 is an exploded front, elevational, sectional view of the mini-condyle prosthesis shown ready to be mounted on the remaining stump of the excised condyle.

For added protection, and in the event that the topography of one or both of the stump's cut surfaces 54 and 55 are irregular, it is preferable to coat at least inferior face 56 with a suitable biocompatible porous coating 58 (FIGS. 5 and 9).

Figure 6:
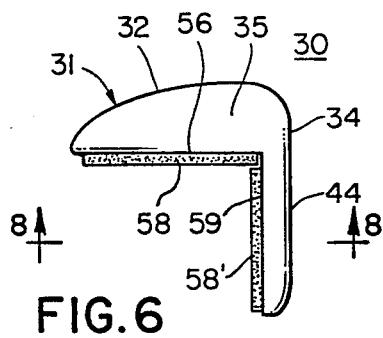
FIG. 6 is a front view in elevation of the mini-condyle prosthesis shown in FIG. 5, and which in addition includes another porous coating on the medial face of the shank.
Figure 7:
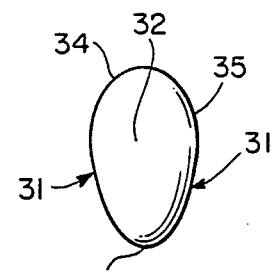
FIG. 7 is a top view of the mini-condyle prosthesis shown in FIG. 6.
Figure 8:
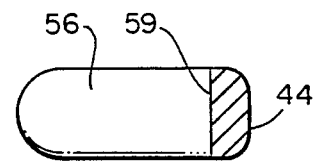
FIG. 8 is bottom plan view of the mini-condyle prosthesis shown in FIG. 1.

In another embodiment FIG. 6), inferior face 56 is coated with porous coating 58 and medial face 59 of shank 44 is also coated with a suitable biocompatible porous coating 58'. Coatings 58 and 58' can be made of the same material or of a different material. Coating 58 and/or coating 58' can be a hard porous ceramic, polymeric, metallic or a composite thereof, such as synthetic hydroxylapatite or porous titanium designed to elicit postoperatively a mechanical, or a mechanical and biochemical fixation bond with the appositional superior cut surface of the remaining living condyle.

Fibrous tissue and/or bone will grow into such porous hard or soft coatings 58 and 58' and will further enhance the fixation bond with appositional bone.

Porous coating 58 and/or coating 58' can also be a suitable biocompatible, tissue ingrowth promoting, soft material which exhibits a compressive stress-strain behavior of a substantially lower order than that of bone. Such a material will deform under load much more readily than its appositional cut surface, so that coating 58 will readily conform to the topography of surface 54 regardless of the irregularities thereof, and will provide a more stable fit between the inferior face 56 of condylar head 31 and superior cut surface 54 of stump 50.

Soft coating 58 or 58' can be porous Teflon. Such material including tissue-ingrowth promoting additives are sold by Vitek, Inc., under said trademark PROPLAST, which has been shown through extensive clinical trials to be biomechanically suitable for this use. The PROPLAST material is soft, very porous, open pore, compressible, and permanently deformable under very slight loads.

The soft porous coating should have a compressibility range between one percent (1%) and forty percent (40%) of its original thickness.

A thickness for the soft coating 58 should be greater than 0.5 mm to provide for an adequate, bio-mechanical, evenly distributed, longitudinal load transfer from condylar head 31 to stump 50 immediately after implantation, thereby strengthening stump 50 to resist load.

Mini prosthesis 30 can be made of a surgical chrome-cobalt-molybdenum alloy, forged cobalt-chrome, or forged titanium.

It may also be formed of sufficiently strong composite structures that combine metal with polymers, or of wholly polymeric structures, which may be reinforced with metal or ceramic or other materials, such as polyamide fiber or carbon fiber.

This invention fills the need for more natural stress and strain patterns within stump 50 by optimizing the conditions for intimate engagement between inferior face 56 of condylar head 31 and the appositional superior cut surface 54 on stump 50.

It will be readily appreciated that mini prosthesis 30 optimizes the TMJ function through improved adaptability during surgery, saves surgical time, saves as much of the natural condyle as possible, provides a more uniform load transfer to the remaining stump of the condyle, allows the oral cavity musculature to function immediately after surgery, and requires only one vertical incision in front of the ear, thereby avoiding the detachment of vital muscles and tissues from the mandible.

By removing the least bone from the natural condyle, stump 50 will have a greater opportunity to withstand normal loads induced therein by the TMJ while it performs its most severe functions as during mastication of hard foods.

What is claimed is:

1. A prosthetic mini-condyle for use with a prosthetic glenoid fossa in the TMJ, said prosthetic fossa covering the natural glenoid fossa and articular eminence, and said mini-condyle covering an excised or deteriorated natural condyle having a superior cut surface and a lateral cut surface; said prosthetic fossa defining an articular, concavo-planar cavity, said mini-condyle comprising:
   a superior, convexo-planar articular face and an inferior flat face;
   a heel extending backwardly, a toe extending forwardly, and an oval sole extending rearwardly between said superior and said inferior faces;
   a shank extending inferiorly from said inferior face and being adapted to become secured to said lateral cut surface;
   said flat inferior face being adapted to abut against said superior cut surface; and
   said condyle, in use, translating and rotating within said fossa cavity so that said superior articular convexo-planar face of said condyle engages said articular concavo-planar cavity and establishes therewith a relatively wide planar contact area which minimizes stress concentrations therebetween.

2. A prosthetic mini-condyle according to claim 1, wherein said inferior flat face has a first coating and said shank has a medial face having a second coating, and said first and second coatings are biocompatible.

3. A prosthetic mini-condyle according to claim 2, wherein said first coating are hard and nondeformable, and said second coating are soft, resilient and deformable.

4. A prosthetic mini-condyle according to claim 2, wherein
   said first coating is soft, resilient and deformable, and said second coating is hard and nondeformable.

5. A prosthetic mini-condyle according to claim 2, wherein said first coating and said second coating are hard and nondeformable.

6. A prosthetic mini-condyle according to claim 2, wherein said first coating and said second coating are soft, resilient and deformable porous and tissue-ingrowth promoting.

7. A prosthetic mini-condyle according to claim 3, wherein said second coating has thickness greater than 0.5 mm.

8. A prosthetic mini-condyle according to claim 4, wherein said first coating has a thickness greater than 0.5 mm.

9. A prosthetic mini-condyle according to claim 3, wherein the porosity of said second coating allows a compression by an amount ranging from one percent (1%) to forty percent (40%) of the original thickness.

10. A prosthetic mini-condyle according to claim 4, wherein the porosity of said first coating allows a compression by an amount ranging from one percent (1%) to forty percent (40%) of the original thickness.

11. A prosthetic mini-condyle according to claim 7, wherein said second coating is a material comprising polytetrafluoroethylene fibers, in admixture with a proportion of carbon or graphite fiber or particles or aluminum oxide particles or synthetic hydroxylapatite particles, and bonded with a sintered polytetrafluoroethylene resin.

12. A prosthetic mini-condyle according to claim 8, wherein said first coating is a material comprising polytetrafluoroethylene fibers, in admixture with a proportion of carbon or graphite fiber or particles or aluminum oxide particles or synthetic hydroxylapatite particles, and bonded with a sintered polytetrafluoroethylene resin, whereby said first coating readily conforms to the topography of said superior cut surface to provide a stable fit between said inferior face and said superior cut surface, and said material encouraging fibrous tissue and bone ingrowth therein for a biological fixation bond between said first coating and said superior cut surface.

13. A prosthetic mini-condyle according to claim 3, wherein said first coating includes synthetic hydroxylapatite or titanium.

14. A prosthetic mini-condyle according to claim 4, wherein said second coating includes synthetic hydroxylapatite or titanium.

15. A prosthetic mini-condyle according to claim 1, wherein said mini-condyle is made of a strong metal, or metal with polymers, or of wholly polymeric structures, or reinforced with metal or ceramic fiber.

* * * * *